(12) United States Patent
Dolla

(10) Patent No.: US 10,849,737 B2
(45) Date of Patent: Dec. 1, 2020

(54) INTRAOCULAR LENS HAVING HINGED HAPTIC STRUCTURES

(71) Applicant: Novartis AG, Basel (CH)

(72) Inventor: William Jacob Spenner Dolla, Plano, TX (US)

(73) Assignee: Alcon Inc., Fribourg (CH)

( * ) Notice: Subject to any disclaimer, the term of this patent is extended or adjusted under 35 U.S.C. 154(b) by 70 days.

(21) Appl. No.: 16/033,918

(22) Filed: Jul. 12, 2018

(65) Prior Publication Data

US 2019/0021849 A1    Jan. 24, 2019

Related U.S. Application Data

(60) Provisional application No. 62/536,060, filed on Jul. 24, 2017.

(51) Int. Cl.
    *A61F 2/16*            (2006.01)

(52) U.S. Cl.
    CPC ............. *A61F 2/1654* (2013.01); *A61F 2/16* (2013.01); *A61F 2002/1681* (2013.01); *A61F 2220/0025* (2013.01); *A61F 2220/0091* (2013.01); *A61F 2230/0006* (2013.01)

(58) Field of Classification Search
    CPC .... A61F 2/1602; A61F 2/1632; A61F 2/1629; A61F 2002/1681; A61F 2002/1683; A61F 2002/1686; A61F 2002/169; A61F 2002/16905; A61F 2002/169053; A61F 2/1694; A61F 2/1654
See application file for complete search history.

(56) References Cited

U.S. PATENT DOCUMENTS

| | | | | |
|---|---|---|---|---|
| 4,540,417 A | * | 9/1985 | Poler | A61M 31/002 424/429 |
| 6,818,158 B2 | * | 11/2004 | Pham | A61F 2/16 264/2.5 |
| 7,029,497 B2 | * | 4/2006 | Zhang | A61F 2/1613 623/6.37 |
| 8,480,734 B2 | * | 7/2013 | Kellan | A61F 2/1624 623/6.51 |
| 2008/0109077 A1 | * | 5/2008 | Bos | A61F 2/1613 623/6.43 |
| 2010/0286772 A1 | * | 11/2010 | Privat de Fortune | A61F 2/1613 623/6.37 |
| 2014/0277437 A1 | * | 9/2014 | Currie | A61F 2/1624 623/6.37 |

\* cited by examiner

*Primary Examiner* — Brian A Dukert
*Assistant Examiner* — Amanda M Barkan

(57) ABSTRACT

An ophthalmic device includes an optic including an optic axis and a haptic structure coupled with the optic. The haptic structure includes an inner ring comprising a plurality of hinges such that portions of the inner ring reside at different radii from the optic axis. The haptic structure further includes a first loop extending from the inner ring and having two points of connection to the inner ring and a second loop extending from the inner ring and having two points of connection to the inner ring. The second loop is oriented opposite the first loop.

5 Claims, 4 Drawing Sheets

INTRAOCULAR LENS HAVING HINGED HAPTIC STRUCTURES

FIELD

The present disclosure relates generally ophthalmic lenses and, more particularly, to intraocular lenses having hinged haptic structures.

BACKGROUND

Intraocular lenses (IOLs) are implanted in patients' eyes either to replace a patient's lens or to complement the patient's lens. An IOL typically includes an optic and haptics. The optic, or lens, corrects the patient's vision typically via refraction or diffraction. Haptics are support structures that hold the optic in place within the capsular bag of a patient's eye. In some cases, haptics take the form of arms that are coupled to the optic. The haptics and optic are generally formed of the same flexible optical material.

In general, a physician selects an IOL for which the optic has the appropriate corrective characteristics for the patient. During ophthalmic surgery, often performed for other conditions such as cataracts, the surgeon implants selected IOL. To do so, the surgeon makes an incision in the capsular bag of the patient's eye and inserts the IOL through the incision. Typically, the IOL is folded or otherwise collapsed to a smaller volume for implantation. The surgeon unfolds or expands the IOL once the IOL is in place. The arms of the haptic expand such that a small section of each arm bears on the capsular bag, retaining the IOL in place. The surgeon then closes the incision.

To function acceptably, the IOL is desired to meet certain specifications. For example, the desired mechanical properties of an IOL are generally expressed in terms of the IOL's force displacement curve. In addition to an acceptable force displacement curve, vaulting should be within specified limits. Vaulting is the movement of the optic along the optic axis in response to radial and/or axial compression. The IOL should also be stable against rotations once implanted within the capsular bag.

Even if the above specifications are met, the IOL may have shortcomings. IOLs may cause striae, or folds, in the posterior capsular bag. The structure of the haptics may exacerbate the formation of striae. For example, the arms of some haptics may contact the capsular bag for only a very small angle. Consequently, more striae may be formed. Striae in the capsular bag may result in posterior capsular opacification (PCO) by providing a mechanism for the growth and/or migration of cells. A mechanism for addressing PCO is thus desired.

Accordingly, what is needed is an improved IOL that may address PCO while maintaining the desired mechanical characteristics.

SUMMARY

An ophthalmic device includes an optic including an optic axis and a haptic structure coupled with the optic. The haptic structure includes an inner ring comprising a plurality of hinges such that portions of the inner ring reside at different radii from the optic axis. The haptic structure further includes a first loop extending from the inner ring and having two points of connection to the inner ring and a second loop extending from the inner ring and having two points of connection to the inner ring. The second loop is oriented opposite the first loop.

In certain embodiments, the ophthalmic device described herein may have one or more technical advantages. For example, the closed-loop haptic structure of the ophthalmic device described herein may result in fewer striae and reduced PCO, yet may be relatively easily implanted. Consequently, performance of the ophthalmic device may be improved.

BRIEF DESCRIPTION OF THE DRAWINGS

For a more complete understanding of the present disclosure and the advantages thereof, reference is now made to the following description taken in conjunction with the accompanying drawings in which like reference numerals indicate like features and wherein.

DETAILED DESCRIPTION

The exemplary embodiments relate to ophthalmic devices such as intraocular lenses (IOLs). The following description is presented to enable one of ordinary skill in the art to make and use the invention and is provided in the context of a patent application and its requirements. Various modifications to the exemplary embodiments and the generic principles and features described herein will be readily apparent. Phrases such as "exemplary embodiment", "one embodiment" and "another embodiment" may refer to the same or different embodiments as well as to multiple embodiments. The embodiments will be described with respect to systems and/or devices having certain components. However, the systems and/or devices may include more or less components than those shown, and variations in the arrangement and type of the components may be made without departing from the scope of the invention. Thus, the present invention is not intended to be limited to the embodiments shown, but is to be accorded the widest scope consistent with the principles and features described herein.

In general, the present disclosure relates to an ophthalmic device includes an optic including an optic axis and a haptic structure coupled with the optic. The haptic structure includes an inner ring comprising a plurality of hinges such that portions of the inner ring reside at different radii from the optic axis. The haptic structure further includes a first loop extending from the inner ring and having two points of connection to the inner ring and a second loop extending from the inner ring and having two points of connection to the inner ring. The second loop is oriented opposite the first loop.

Figure 1A:
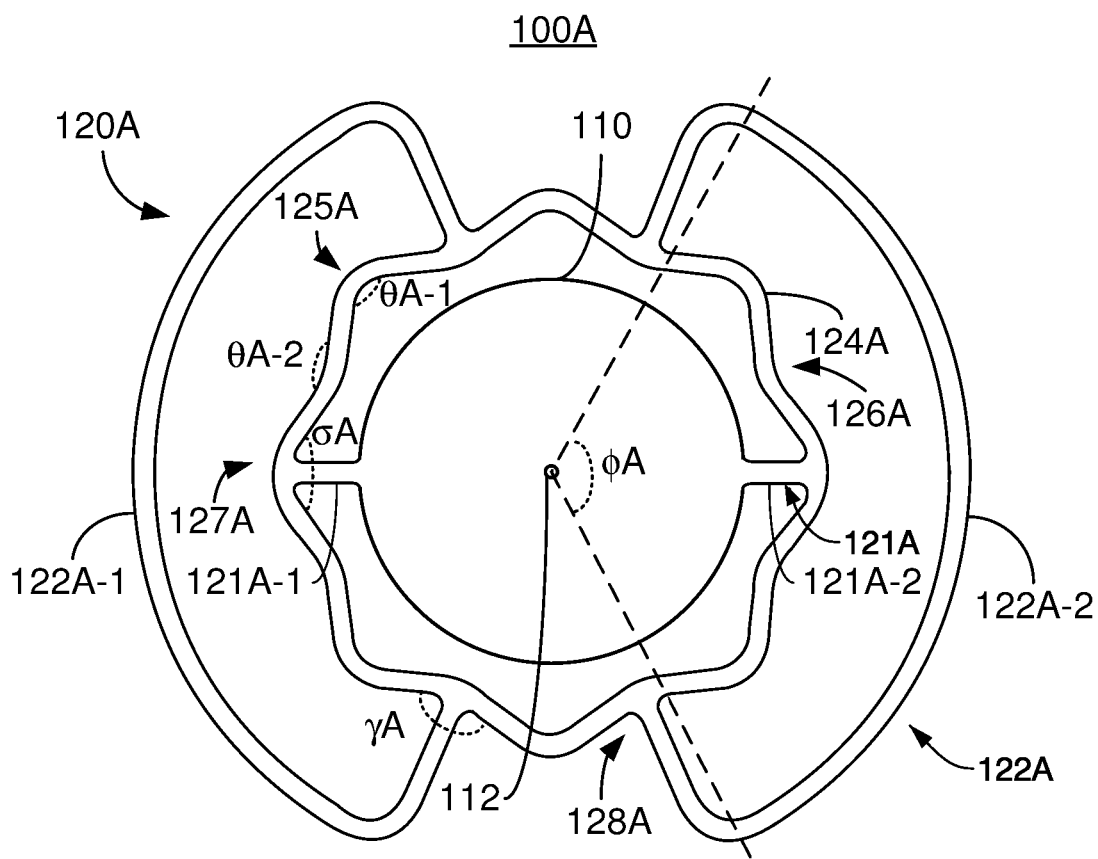
FIGS. 1A-1B depict plan and side views of an exemplary embodiment of an ophthalmic device having a hinged closed-loop haptic structure.
Figure 1B:
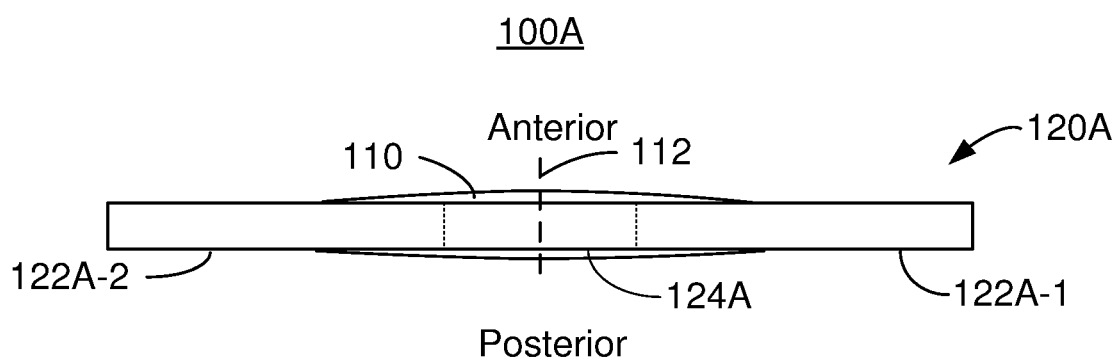

FIGS. 1A-1B depict plan and side views, respectively, of an exemplary embodiment of an ophthalmic device 100A having an optic 110 and a hinged closed-loop haptic structure 120A. For simplicity, the ophthalmic device 100A is also referred to as an IOL 100A. For clarity, FIGS. 1A-1B are not to scale and not all components may be shown.

The optic 110 is an ophthalmic lens 110 that may be used to correct a patient's vision. For example, the optic may be a refractive and/or diffractive lens. The optic 110 may be a monofocal lens, a multifocal lens, a toric lens, or any other suitable type of lens. The anterior and/or posterior surface of the optic 110 may have features including but not limited to a base curvature and diffraction grating(s). The optic 110 may refract and/or diffract light to correct the patient's vision. The optic 110 has an optic axis 112 that is out of the plane of the page in FIG. 1A. The optic 110 is depicted as having a circular footprint in the plan view of FIG. 1A. In other embodiments, the optic 110 may have a differently shaped footprint. In some embodiments, the optic 110 may also include other features that are not shown for clarity. The optic 110 may be formed of one or more of a variety of flexible optical materials. For example, the optic 110 may include but is not limited to one or more of silicone, a hydrogel and an acrylic such as AcrySof®.

In some embodiments, the optic 110 may be surrounded by another ring, or frame, (not shown) at the periphery of the optic 110. Such a frame would be part of the hinged haptic structure 120A and would couple the hinged haptic structure haptic 120A with the optic 110. The inner portion of such frame would be desired to match the shape of the optic 110. In other embodiments, such as that shown in FIGS. 1A-1B, the frame may be omitted. In some embodiments, the hinged haptic structure 120A and the optic 110 may be molded together. Thus, the optic 110 and haptic 120A may form a single monolithic structure. In other embodiments, the hinged haptic structure 120A may be otherwise attached to the optic 110. For example, the hinged haptic structure 120A may be bonded to or molded around a preexisting optic 110.

The hinged haptic structure 120A is a support structure used to hold the ophthalmic device 100A in place in the capsular bag of a patient's eye (not explicitly shown). The hinged closed-loop haptic structure 120A includes closed loops 122A-1 and 122A-2 (collectively 122), inner ring 124A and hinges 125A and 126A (of which only one of each is labeled for simplicity). Also shown are joints 127A and 128A of which only one of each is labeled for clarity. As used herein, a hinge is a connection point between two connectors, or members. A joint is a connection point between three or more connectors/members. A member or connector is substantially straight and/or has a radius of curvature significantly greater than that of a corresponding hinge. For example, the radius of curvature of a member may be at least twice that of a hinge. Joints 127A are between the inner ring 124A and the struts 129 connecting the inner ring 124A to the optic 110. Joints 128A are between the inner ring 124A and the outer loops 122.

In the embodiment shown in FIGS. 1A-1B, the inner ring 124A is connected to the optic 110 via struts 121A-1 and 121A-2 (collectively 121). In another embodiment, another number of struts 121 might be used. For example, three, four, five or six struts might be present. In another embodiment, the inner ring 124A is directly connected to the optic 110. For example, portions of the hinges 126A that are closest to the optic 110 may be bonded to or molded with the optic 110. In such a case, the struts 121 may but need not be omitted.

The hinges 125A and 126A are part of the inner ring 124. Hinges 125A connect members extending outward from the optic 110 and thus are further from the optic 110 than hinges 126A. In contrast, hinges 126A connect members extending inward toward the optic 110. When hinged haptic structure 120A is compressed, the hinges 126A may move toward the optic 110, while the hinges 125A may move away from the optic 110. Thus, the angles θA-1 and θA-2 decrease in size when the hinged haptic structure 120A is compressed. Joints 127A and 128A are not expected to move substantially under lower compressive forces. The flexibility of the hinges 125A and 126A may be tailored by configuring the cross-sectional area of the hinges 125A and 126A and the material(s) used for the hinges 125A and 126A. The flexibility of the joints 127A and 128A may be adjusted using similar parameters. Because the joints 127A and 128A occur at the intersection of a larger number of members, the joints 127A and 128A are generally less flexible than the hinges 125A and 126A.

The inner ring 124 has an undulating, or wavy, periphery because of the presence of the hinges 125A and 126A and joints 127A and 128A. For example, the shape of the inner ring 124 might be described by a sinusoidal curve or other function having a varying amplitude. Thus, the hinges 125A may correspond to maxima for the sinusoidal curve, while the hinges 126A may be the minima. Although a certain number of hinges 125A and 126A (maxima/minima) are shown, another number may be present. Although a smoothly varying periphery is shown, the periphery may vary in a sharp and/or discontinuous transitions. For example, one or more of the hinge(s) 125A and/or 126A may be a sharp corner instead of a curve. In the embodiment shown, each of the hinges 125A, 126A and joints 127A and 128A subtend substantially the same angle when uncompressed. Thus, the angles θA-1, θA-2, σA and γA are substantially the same. In other embodiments, one or more of the angles θA-1, θA-2, σA and γA may differ.

The closed loops 122A hold the IOL 100A in position in the patient's eye by bearing on the capsular bag. Each of the loops 122A subtends a large angle, φA. This angle φA is greater than ninety degrees in some embodiments. For example, the angle φA may be at least one hundred and twenty degrees in some cases. Consequently, the loops 122A contact the capsular bag over a large angle. The capsular bag may thus be extended over a larger volume. The loops 122A-1 and 122A-2 may thus stretch the capsular bag over a significantly larger region than for haptics having open arms. Further, the contact force between the capsular bag and the closed loops 122A may be more uniform along the loops 122A. These features may reduce striae and, therefore, PCO.

The hinged haptic structure 120A may also have one or more sharp edges. As depicted in FIG. 1B, the loops 122A have sharp outside corners. The inner ring 124A may have sharp outside corners (at the outer surface of the ring 124A) and/or sharp inside corners (at the inner surface of the ring 124A). The optic 110 might have sharp corners (not shown). As a result, the optic 110 may be surrounded on all sides by sharp edges. These sharp edges may also reduce the probability of cells migrating to the optic 110 from any side. PCO may be reduced or eliminated.

Use of the IOL 100A may improve patient outcomes. The stiffness of the hinged closed-loop haptic structure 120A can be tailored using the number of hinges and/or joints, the cross-sectional area of the hinges and/or joints and material(s) used for the hinges and/or joints. Thus, the response to a radial force, force displacement curve, axial (along the optic axis 112) stiffness, vaulting and other mechanical properties can be tailored to the desired specifications for the IOL 100A. The angles θA-1 and θA-2 decrease in size and the hinges 125A and 126A move radially when the hinged haptic structure 120A is compressed. The inner ring 124A and loops 122A tend to remain substantially in the same plane when under compression. Consequently, vaulting may be reduced and movement of the hinged haptic structure 120A may be more predictable. The large angle ϕA subtended by the closed loops 122A allows the closed-loop haptic structure to contact a larger portion of and better extend the capsular bag. The contact force between the closed loops 122A and capsular bag may also be more uniform. This may not only improve the axial and rotational stability of the IOL 100A, but also reduce the formation of striae (wrinkles) in the capsular bag. PCO may thus be mitigated or prevented. Sharp edges for the hinged closed-loop haptic structure 120A may further reduce PCO.

Figure 2:
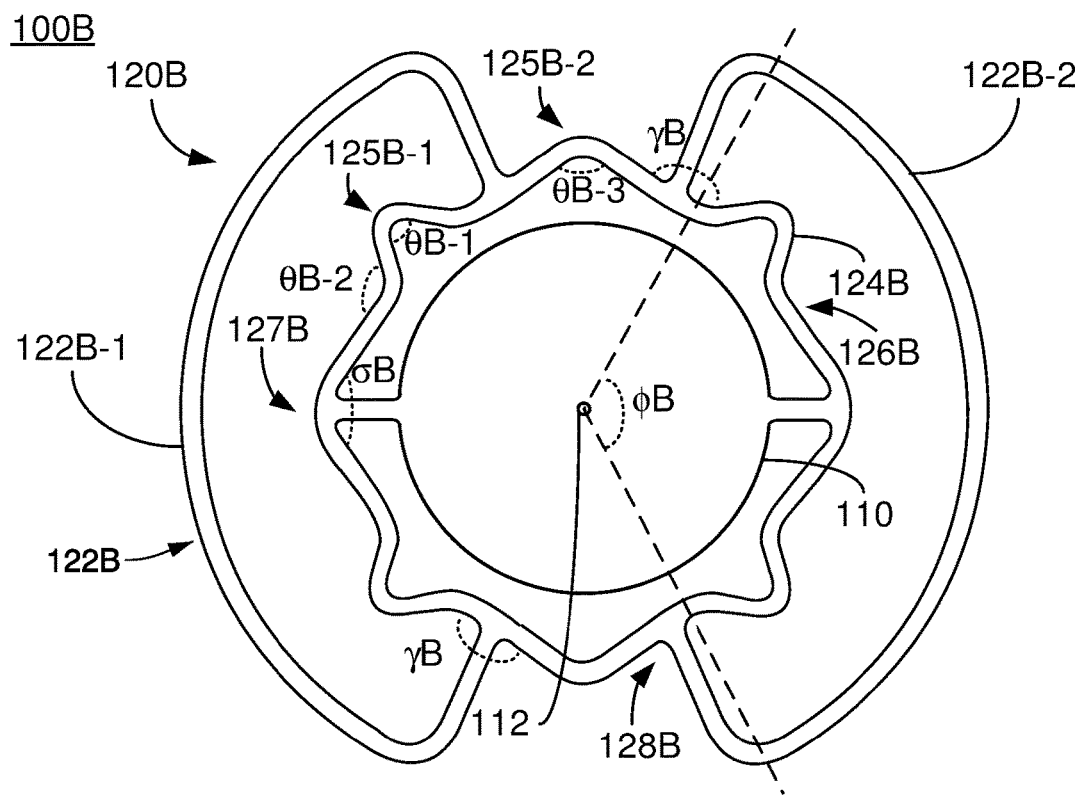
FIG. 2 depicts another exemplary embodiment of an ophthalmic device having a hinged closed-loop haptic structure.

FIG. 2 depicts another exemplary embodiment of an ophthalmic device 100B having an optic 110 and a hinged closed-loop haptic structure 120B. For simplicity, the ophthalmic device 100B is also referred to as an IOL 100B. The IOL 100B is analogous to the IOL 100A. Consequently, analogous components have similar labels. Thus, the IOL 100B includes an optic 110 and closed-loop haptic structure 120B that are analogous to the optic 110 and closed-loop haptic structure 120A. For clarity, FIG. 2 is not to scale and not all components may be shown.

The optic 110 may be a refractive and/or diffractive lens and may be monofocal, multifocal and/or toric. The hinged closed-loop haptic structure 120B includes closed loops 122B-1 and 122B-2 (collectively 122B), inner ring 124B, hinges 125B-1.125B-2 and 126B and joints 127B and 128B that are analogous to closed loops 122A, inner ring 124A, hinges 125A and 126A and joints 127A and 128A, respectively.

The IOL 100B functions in an analogous manner to and shares analogous benefits with the IOL 100A. However, the angles subtended by the hinges 125B-1 and 125B-2 differ. Similarly, the angles subtended by the hinges 125B-1 and 126B differ. Thus, θB-1 differs from θB-2 and θB-3. The angles subtended by the hinges 125B-1 and the joints 127B and 128B also differ. Thus, θB-1 differs from σB and γB. Consequently, the response of the hinged haptic structure 120B may differ from that of the hinged haptic structure 120A. For example, the inner ring 124B may not react symmetrically to a symmetric radial compressive force. However, the benefits of the hinged haptic structure may be maintained. For example, the response to a radial force, force displacement curve, axial stiffness, vaulting and other mechanical properties can be tailored to the desired specifications for the IOL 100B. Vaulting may be reduced and movement of the hinged haptic structure 120B may be more predictable. The large angle ϕB subtended by the closed loops 122B allows the closed-loop haptic structure to contact a larger portion of and better extend the capsular bag. The contact force between the closed loops 122B and capsular bag may also be more uniform. This may not only improve the axial and rotational stability of the IOL 100B, but also reduce the formation of striae in the capsular bag. PCO may thus be mitigated or prevented. Sharp edges for the hinged closed-loop haptic structure 120B may further reduce PCO.

Figure 3:
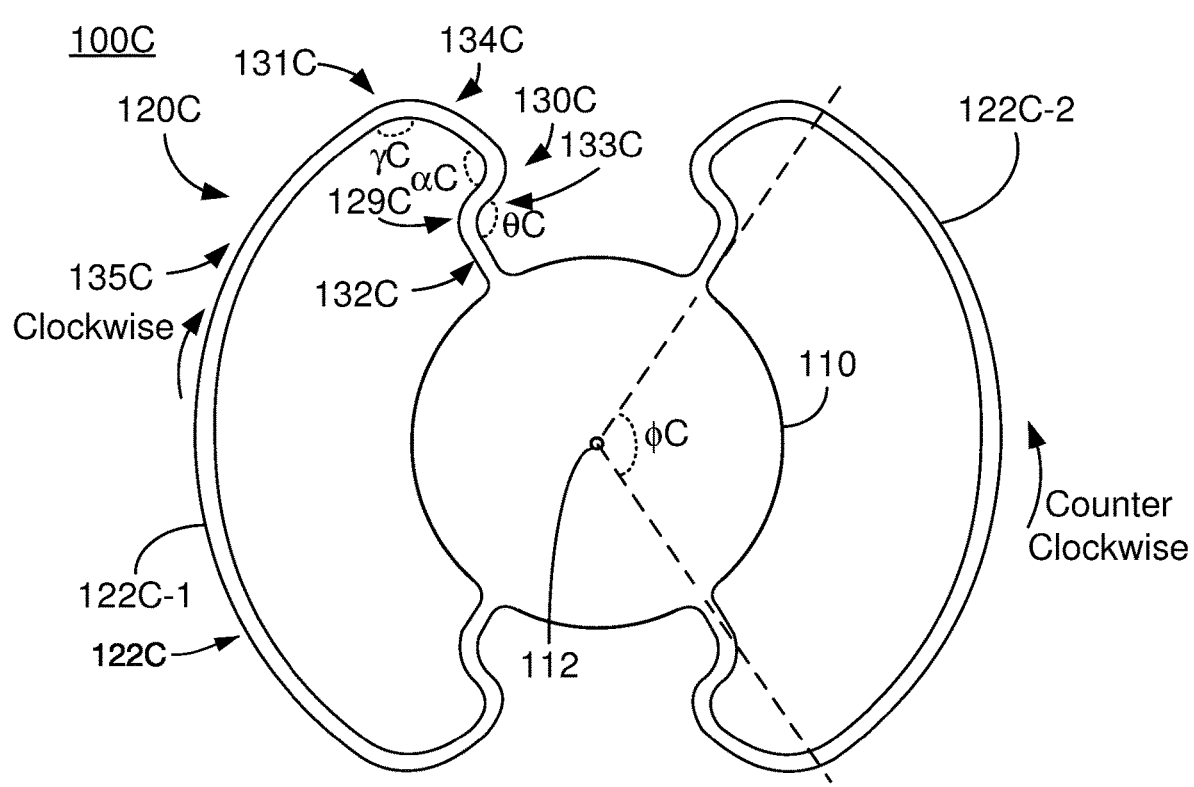
FIG. 3 depicts another exemplary embodiment of an ophthalmic device having a hinged closed-loop haptic structure.

FIG. 3 depicts another exemplary embodiment of an ophthalmic device 100C having an optic 110 and a hinged closed-loop haptic structure 120C. For simplicity, the ophthalmic device 100C is also referred to as an IOL 100C. The IOL 100C is analogous to the IOL(s) 100A and/or 100B. Consequently, analogous components have similar labels. Thus, the IOL 100C includes an optic 110 and closed-loop haptic structure 120C that are analogous to the optic 110 and closed-loop haptic structure(s) 120A and 120B. For clarity, FIG. 2 is not to scale and not all components may be shown.

The optic 110 may be a refractive and/or diffractive lens and may be monofocal, multifocal and/or toric. In some embodiments, the optic 110 may be surrounded by another ring, or frame, (not shown) at the periphery of the optic 110. Such a frame would be part of the hinged haptic structure 120C and would couple the hinged haptic structure haptic 120C with the optic 110. The inner portion of such frame would be desired to match the shape of the optic 110. In other embodiments, such as that shown in FIG. 3, the frame is omitted. In some embodiments, the hinged haptic structure 120C and the optic 110 may be molded together. Thus, the optic 110 and haptic 120C may form a single monolithic structure. In other embodiments, the hinged haptic structure 120C may be otherwise attached to the optic 110. For example, the hinged haptic structure 120C may be bonded to or molded around a preexisting optic 110.

The hinged closed-loop haptic structure 120C includes closed loops 122C-1 and 122C-2 (collectively 122C), hinges 129C, 130C and 131C and connectors 132C, 133C, 134C and 135C. For clarity, only one of each hinge and connector is labeled. However, each loop 122C may include two of each of the hinges 129C, 130C and 131C and connectors 132C, 133C, and 134C. The hinges 129C, 130C and 131C are analogous to the hinges 125A, 126A, 125B and 126B in that two connectors meet at each hinge 129C, 130C and 131C. Although two loops 122C are shown, in another embodiment, another number of loops might be used.

The closed loops 122C retain the IOL 100C in position in the patient's eye by bearing upon the capsular bag. Each of the loops 122C subtends a large angle, ϕC. The angle ϕC is analogous to the angles ϕA and ϕB. For a larger number of loops, each loop may subtend a smaller angle. However, because there would be more loops, the total angle subtended by the loops would still be large. Consequently, the loops 122C contact the capsular bag over a significantly larger angle than for haptics having open arms. As a result, stability may be enhanced and formation of striae reduced. In addition, although not shown in FIG. 3, the loops 122C may have sharp edges. In this manner, the loops 122C may be analogous to the loops 122A and 122B and inner rings 124A and 124B.

The connectors 132C and 134C are radial connectors, while the connectors 133C and 135C are axial connectors. The radial connectors 132C and 134C extend primarily in the radial direction (outward from the optic 110/optic axis 112). Stated differently, the radial connectors 132C and 134C are less than forty-five degrees from the radial direction. The axial connectors 133C and 135C extend primarily around the optic axis 112, in the clockwise and/or counter-clockwise direction. Thus, the axial connectors 133C and 135C are less than forty-five degrees from the clockwise/counter-clockwise directions.

The radial connectors 132C and 134C and axial connectors 133C and 135C alternate, with hinges 129C, 130C and 131C located where the connectors join. Thus, the first radial connector 132C is coupled with the optic 110. In some embodiments, the radial connector 132C is molded with the optic 110. In other embodiments, the radial connector 132C is bonded to the optic 110. The hinge 129C connects the radial connector 132C and the axial connector 133C. The hinge 130C connects the axial connector 133C to the radial connector 134C. The radial connector 134C and the axial connector 135C are coupled via the hinge 131C. As a result, the hinge 130C and radial connector 134C are on one side of the radial connector 132C, while most or all of the axial connector 135C is on the opposite side of the radial connector 132C. For example, for the items labeled in FIG. 3, the radial connector 134C is clockwise from the radial connector 132C, while most of the axial connector 135C is counter-clockwise from the radial connector 132C. In addition, the radial connector 134C is further from the optic axis 112 than the radial connector 132C. The connection of each loop 122C to the optic 110 is completed using an analogous series of radial connectors, axial connectors and hinges. As a result, one or more of the loops 122C has a portion that extends past the attachment point to the optic 110.

Because of the configuration of the loops 122C, the radial connectors 134C tend to move perpendicular to the radial direction when placed under compression. The axial connectors 135C move in the radial direction toward the optic 110 when under the same compression. As a result, the haptic 120C tends to remain substantially in plane when compressed.

The IOL 100C may share many of the benefits of the IOLs 100A and/or 100B. The response to a radial force, force displacement curve, axial stiffness, vaulting and other mechanical properties can be tailored to the desired specifications for the IOL 100C. This may be accomplished using the cross-sectional area and materials for each of the hinges and connectors in the loops 122C. The configuration of the hinges 129C, 130C and 131C as well as the connectors 132C, 133C, 134C and 135C may allow a predictable compression of the loops 122C that remains substantially in the plane of the optic 110. The large angle ϕC subtended by the closed loops 122C allows the closed-loop haptic structure to contact a larger portion of and better extend the capsular bag. The contact force between the closed loops 122C and capsular bag may also be more uniform. This may not only improve the axial and rotational stability of the IOL 100C, but also reduce the formation of striae in the capsular bag. PCO may thus be mitigated or prevented. Sharp edges for the hinged closed-loop haptic structure 120C may further reduce PCO.

Figure 4A:
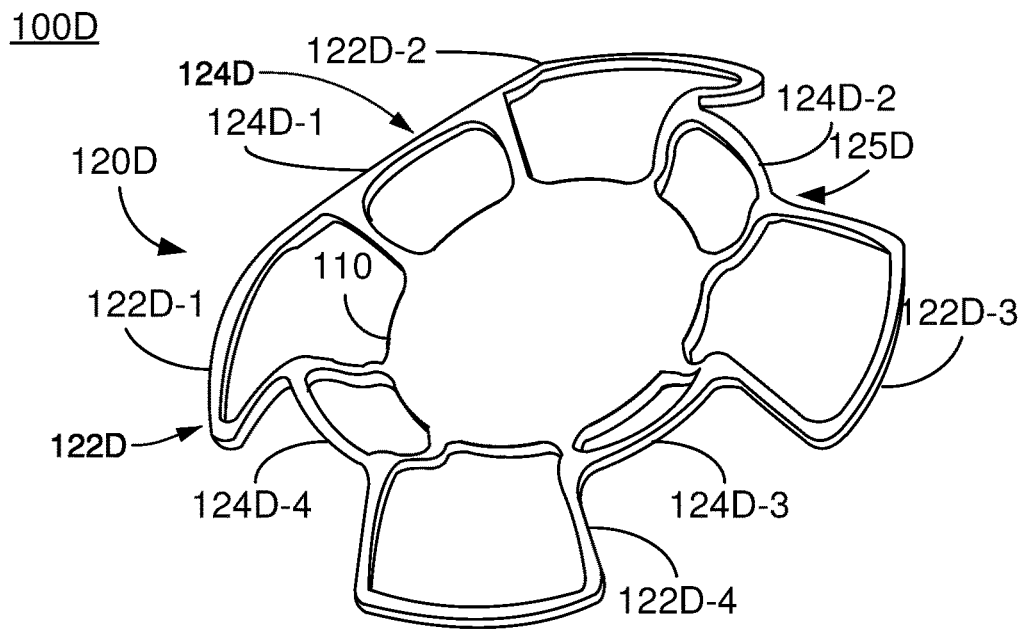
FIGS. 4A-4C depict another exemplary embodiment of an ophthalmic device having a hinged, three-dimensional closed-loop haptic structure.
Figure 4B:
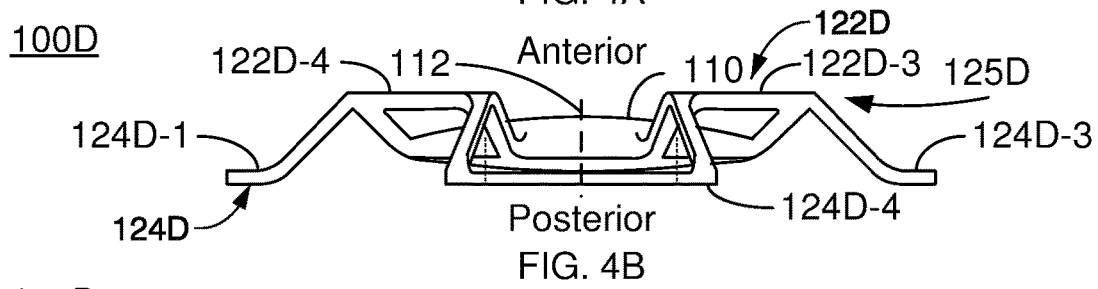
Figure 4C:
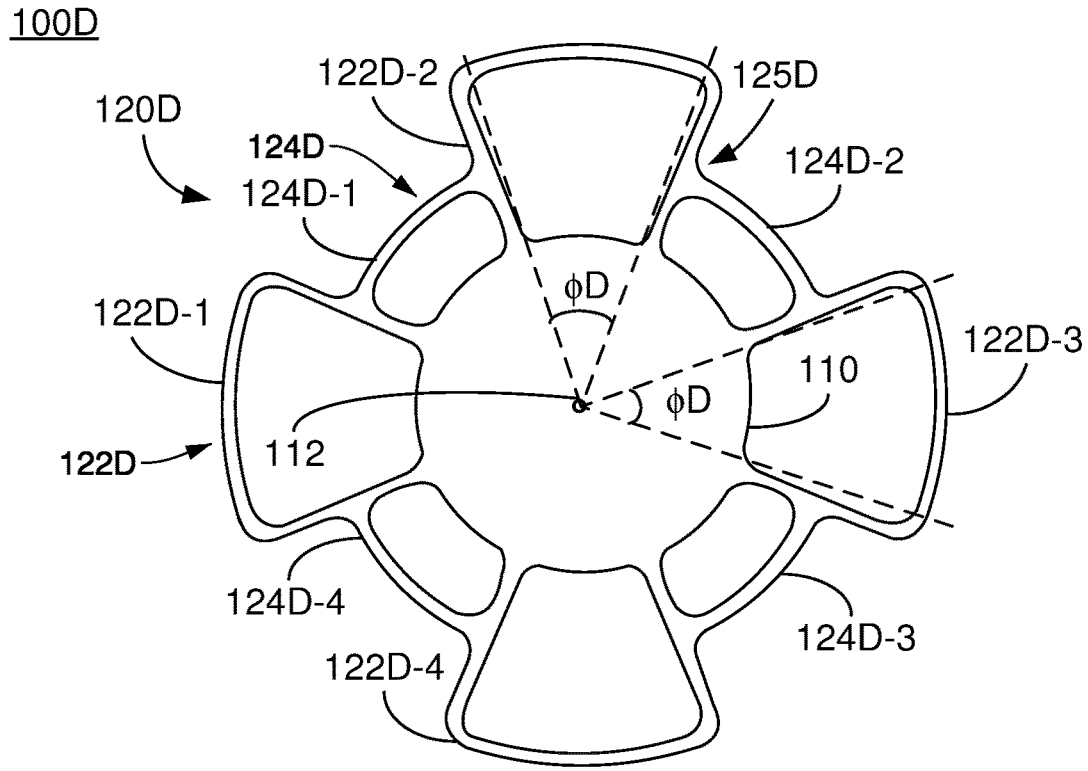

FIGS. 4A-4C depict another exemplary embodiment of an ophthalmic device 100D having an optic 110 and a hinged closed-loop haptic structure 120D. For simplicity, the ophthalmic device 100D is also referred to as an IOL 100D. FIGS. 4A, 4B and 4C depict perspective, side and plan views, respectively, of the IOL 100D. The IOL 100D is analogous to the IOLs 100A, 100B and 100C. Consequently, analogous components have similar labels. Thus, the IOL 100D includes an optic 110 and hinged closed-loop haptic structure 120D that are analogous to the optic 110 and closed-loop haptic structures 120A, 120B and 120C. For clarity, FIGS. 4A-4C are not to scale and not all components may be shown.

The optic 110 may be a refractive and/or diffractive lens and may be monofocal, multifocal and/or toric. In some embodiments, the optic 110 may be surrounded by another ring, or frame, (not shown) at the periphery of the optic 110. Such a frame would be part of the hinged haptic structure 120D and would couple the hinged haptic structure haptic 120D with the optic 110. The inner portion of such frame would be desired to match the shape of the optic 110. In other embodiments, such as that shown in FIGS. 4A-4C, the frame is omitted. In some embodiments, the hinged haptic structure 120D and the optic 110 may be molded together. Thus, the optic 110 and haptic 120D may form a single monolithic structure. In other embodiments, the hinged haptic structure 120D may be otherwise attached to the optic 110. For example, the hinged haptic structure 120D may be bonded to or molded around a preexisting optic 110.

The hinged haptic structure 120D includes loops 122D-1, 122D-2, 122D-3 and 122D-4 (collectively 122D), axial connectors 124D-1, 124D-2, 124D-3 and 124D-4 (collectively 124D) and hinges 125D (of which only one is labeled). The loops 122D and hinges 125D are analogous to the loop(s) 122A, 122B and/or 122C and hinges 125A and/or 125B. The axial connectors 122D may be viewed as forming an inner ring analogous to the ring(s) 122A and/or 122B. Alternatively, the loops 122D and axial connectors 124D may be viewed as being formed of two alternating trapezoidal unit cells with one having a larger outside radius (loops 122D) and one have a smaller outside radius (axial connectors 122D).

The loops 122D hold the IOL 100D in place in the patient's eye by bearing upon the capsular bag. Each of the loops 122D subtends an angle, ϕD. The total angle subtended (four multiplied by ϕD) is large in comparison to that for haptics having open arms. Thus, the loops 122H may stretch the capsular bag to a greater extent than an open arm haptic, improving stability and reducing striae. Although four loops 122D are shown, another number may be used in a different embodiment. Further, the loops 122D may subtend different angles in other embodiments. For example, the loops 122D-2 and 122D-4 may have a larger angle than the loops 122D-1 and 122D-3. Alternatively, the loops 122D-1 and 122D-3 may subtend a larger angle than the loops 122D-2 and 122D-4.

In the embodiment shown, the loops 122D have a component parallel to the optic axis 112. Thus, the hinged closed-loop haptic structure 120D may be viewed as a three-dimensional structure. Because the loops 122D have components along the optic axis 112, the hinged haptic structure 120D may extend the capsular bag not only radially, but also along the optic axis 112 (e.g. out of the plane of the page in FIG. 4C). The hinged closed-loop haptic structure 120D may be better able to keep the capsular bag open. Stated differently, the three-dimensional nature of the haptic structure 120D may keep the capsular bag open not only axially and radially in the plane shown in FIG. 4C, but also along the optic axis 112. In the embedment shown, the loops 122D have components parallel to the optic axis 112 both anterior and posterior to the optic 112. Stated differently, the outer edge of the loops 122D are on the posterior side of the optic 110 while the connectors 124D (middle portions of the loops 122D) are on the anterior side of the optic 110. In other embodiments, this situation might be reversed. Alternatively, the loops 122D may extend only on the posterior side or only on the anterior side of the optic. In other embodiments, the loops 122D may be substantially planar. In such an embodiment, the side view of the IOL 100D may be similar to that of the IOL 100A. However, such an embodiment may be less successful in extending the capsular bag along the optic axis.

The mechanical stiffness and other properties of the hinged closed-loop haptic structure 120D may be tailored by configuring the hinges 125D, connectors 124D and loops 122D. For example, the axial stiffness, response to a radial force and force displacement curve may be tailored by changing the number, cross-sectional area and material(s) used for the hinges 125D, loops 122D and connectors 124D.

The IOL 100D may share many of the benefits of the IOLs 100A, 100B and/or 100C. The response to a radial force, force displacement curve, axial stiffness, vaulting and other mechanical properties can be tailored to the desired specifications for the IOL 100D. This may be accomplished using the cross-sectional area and materials for each of the hinges and connectors in the loops 122C. The large angle 4ϕD subtended by the closed loops 122D allows the closed-loop haptic structure to contact a larger portion of and better extend the capsular bag. The contact force between the closed loops 122D and capsular bag may also be more uniform. The closed loops 122D may also extend the capsular bag along the optic axis 112 in addition to expanding the capsular bag radially and axially. This may not only improve the axial and rotational stability of the IOL 100D, but also reduce the formation of striae in the capsular bag. The three-dimensional configuration of the haptic 120D may be better able to keep the capsular bag open while maintaining contact pressure between the IOL 100D and the capsular bag. This may reduce postoperative cellular proliferation and/or reactivity. PCO may thus be mitigated or prevented. Sharp edges for the hinged closed-loop haptic structure 120D may further reduce PCO.

Figure 5:
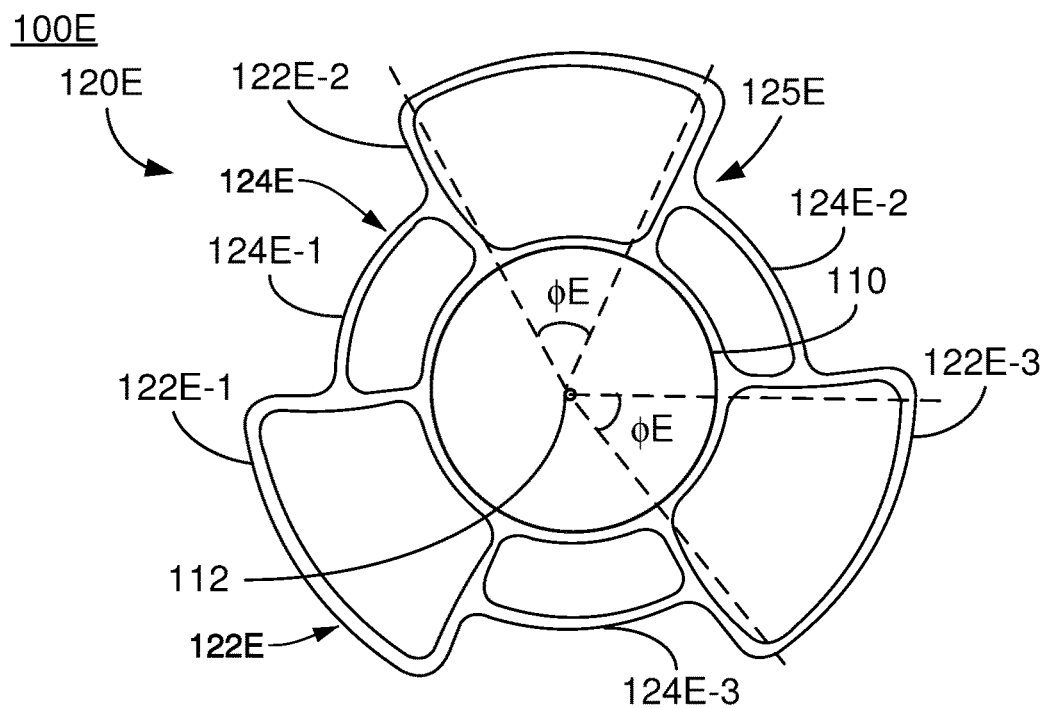
FIG. 5 depicts another exemplary embodiment of an ophthalmic device having a hinged, three-dimensional closed-loop haptic structure.

FIG. 5 depicts another exemplary embodiment of an ophthalmic device 100E having an optic 110 and a hinged closed-loop haptic structure 120E. For simplicity, the ophthalmic device 100E is also referred to as an IOL 100E. The IOL 100E is analogous to the IOLs 100A, 100B, 100C and 100D. Consequently, analogous components have similar labels. Thus, the IOL 100E includes an optic 110 and hinged closed-loop haptic structure 120E that are analogous to the optic 110 and closed-loop haptic structures 120A, 120B, 120C and 120D. For clarity, FIG. 5 are not to scale and not all components may be shown.

The IOL 100E is most analogous to the IOL 100D. The IOL 100E includes optic 110 and hinged haptic structure 120E including loops 122E-1, 122E-2 and 122E-3 (collectively 122E), axial connectors 124E-1, 124E-2 and 124E-3 (collectively 124E) and hinges 125E (of which only one is labeled) that are analogous to optic 110 and hinged haptic structure 120E including loops 122D, axial connectors 124D and hinges 125D. The loops 122D and hinges 125D are analogous to the loop(s) 122A, 122B and/or 122C and hinges 125A and/or 125B.

The optic 110 is analogous to those previously discussed. The functions of the loops 122E and axial connectors 124E are analogous to those of the loops 122D and axial connectors 124D. However, only three loops 122E are present instead of four. The loops 122E are still distributed evenly around the optic 110 and subtends an angle per loop of, ϕE. In other embodiments, the loops 122E need not be evenly distributed and/or may subtend different angles in other embodiments.

The IOL 100E may share many of the benefits of the IOLs 100A, 100B, 100C and/or 100D. The response to a radial force, force displacement curve, axial stiffness, vaulting and other mechanical properties can be tailored to the desired specifications for the IOL 100E. This may be accomplished using the cross-sectional area and materials for each of the hinges and connectors in the loops 122E. The large angle 34E subtended by the closed loops 122E allows the closed-loop haptic structure to contact a larger portion of and better extend the capsular bag. The contact force between the closed loops 122E and capsular bag may also be more uniform. In addition, the closed loops 122E may extend the capsular bag along the optic axis 112. This may not only improve the axial and rotational stability of the IOL 100E, but also reduce the formation of striae in the capsular bag. The three-dimensional configuration of the haptic 120E may be better able to expand the capsular bag while maintaining contact pressure between the IOL 100E and the capsular bag. PCO may thus be mitigated or prevented. Sharp edges for the hinged closed-loop haptic structure 120E may further reduce PCO.

Figure 6:
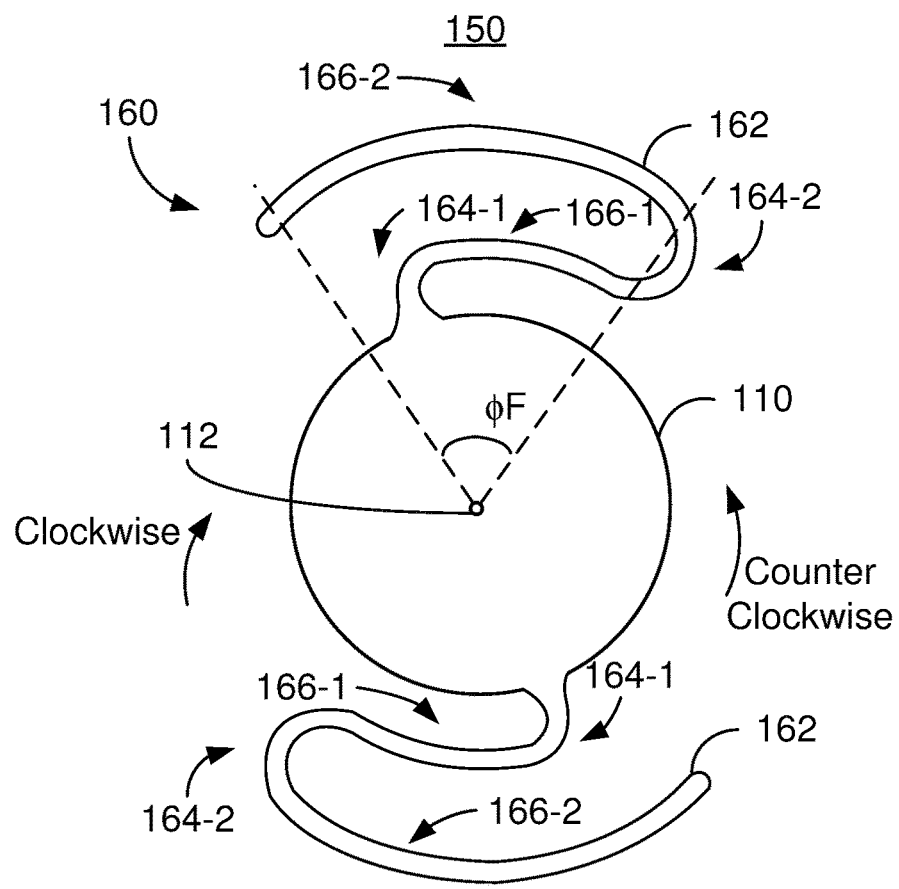
FIG. 6 depicts another exemplary embodiment of an ophthalmic device having a hinged haptic structure; and The skilled person in the art will understand that the drawings, described below, are for illustration purposes only. The drawings are not intended to limit the scope of the applicant's disclosure in any way.

FIG. 6 depicts another exemplary embodiment of an ophthalmic device 150 having an optic 110 and a hinged haptic structure 160. For simplicity, the ophthalmic device 150 is also referred to as an IOL 150. The IOL 150 is analogous to the IOLs 100A, 100B, 100C and 100D in that the IOL 150 has a hinged haptic structure. However, the hinged haptic structure 160 is not a closed-loop haptic structure.

The optic 110 may be a refractive and/or diffractive lens and may be monofocal, multifocal and/or toric. In some embodiments, the optic 160 may be surrounded by another ring, or frame, (not shown) at the periphery of the optic 160. Such a frame would be part of the hinged haptic structure 160 and would couple the hinged haptic structure haptic 160 with the optic 110. The inner portion of such frame would be desired to match the shape of the optic 110. In other embodiments, such as that shown in FIG. 6, the frame is omitted. In some embodiments, the hinged haptic structure 160 and the optic 110 may be molded together. Thus, the optic 110 and haptic 160 may form a single monolithic structure. In other embodiments, the hinged haptic structure 160 may be otherwise attached to the optic 110. For example, the hinged haptic structure 120E may be bonded to or molded around a preexisting optic 110.

The hinged haptic structure 160 includes arms 162 having hinges 164-1 and 164-2 (collectively 164) and axial connectors 166-1 and 166-2 (collectively 166). The hinge 164-1 is approximately at the connection to the optic 110. The axial connector 166-1 is between the hinges 164-1 and 164-2. The hinge 164-2 is between the axial connectors 166-1 and 166-2. The hinges 164-1 and 164-2 subtend angles of at least one hundred degrees. In some embodiment, the angles may be at least one hundred twenty degrees. The angles may exceed one hundred fifty degrees. For example, the angles may be nominally one hundred eighty degrees. The hinges 166 may also be curved as shown in FIG. 6. Thus, the hinges 166 may be viewed as semicircular hinges. The axial member 166-2 is further from the optic 110 than the axial member 166-1. From the hinge 164-1 to the outer end of the arms 162, the axial members 166-1 and 166-2 may be seen as extending in the clockwise and counter-clockwise direction, respectively. Additional hinges and axial members (not shown) may be included in other embodiments. The stiffness and other mechanical characteristics of the arms 162 may be tailored using the cross-sectional area of the arms 162 and the hinges 164.

The hinges 166 subtend large angles and the outer connectors 166-2 are substantially perpendicular to the radial direction. The arms 162 thus subtend large angles, ϕF. Consequently, the arms 162 may be better able to fully extend the capsular bag than a conventional haptic.

The IOL 150 may share many of the benefits of the IOLs 100A, 100B, 100C, 100D and/or 100E. The response to a radial force, force displacement curve, axial stiffness, vaulting and other mechanical properties can be tailored to the desired specifications for the IOL 150. This may be accomplished using the cross-sectional area and materials for each of the hinges and connectors in the arms 160. The large angle F subtended by the arms 162 allows the haptic structure to contact a larger portion of and better extend the capsular bag. This may not only improve the axial and rotational stability of the IOL 160, but also reduce the formation of striae in the capsular bag. PCO may thus be mitigated or prevented. Sharp edges for the hinged closed-loop haptic structure 1260 may further reduce PCO.

Various features of the IOLs 100A, 100B, 100C, 100D, 100E and 150 have been described herein. One of ordinary skill in the art will recognize that one or more of these features may be combined in manners not explicitly disclosed herein and that are not inconsistent with the method and apparatus described.

It will be appreciated that various of the above-disclosed and other features and functions, or alternatives thereof, may be desirably combined into many other different devices or applications. It will also be appreciated that various presently unforeseen or unanticipated alternatives, modifications, variations or improvements therein may be subsequently made by those skilled in the art which alternatives, variations and improvements are also intended to be encompassed by the following claims.

The invention claimed is:

1. An ophthalmic device comprising:
   an optic including an optic axis; and
   a haptic structure coupled with the optic, the haptic structure comprising:
      an inner ring comprising a plurality of members and a plurality of hinges connecting the plurality of members, whereby a first portion of the plurality of members extends outward from the optic and a second portion of the plurality of members extends inward toward the optic such that portions of the inner ring reside at different radii from the optic axis;
      a first loop extending from the inner ring and having at least two unique points of connection to the inner ring; and a second loop extending from the inner ring and having at least two unique points of connection to the inner ring, the second loop oriented opposite the first loop.

2. The ophthalmic device of claim 1, further comprising a plurality of struts each extending substantially radially outward from the optic and connecting the optic and the inner ring.

3. The ophthalmic device of claim 2, wherein the plurality of struts are spaced evenly around the periphery of the optic.

4. The ophthalmic device of claim 1, wherein each of the plurality of hinges subtends a first angle, the first angle of each of the plurality of hinges being substantially equal.

5. The ophthalmic device of claim 1, wherein:
   the first loop subtends a first angle;
   the second loop subtends a second angle; and
   the first angle and the second angle have substantially the same value, the value being greater than or equal to ninety degrees.

\* \* \* \* \*